US012569605B2

(12) United States Patent
Karow et al.

(10) Patent No.:  US 12,569,605 B2
(45) Date of Patent:    Mar. 10, 2026

(54) CONTROL DEVICE OR CLOSED-LOOP CONTROL DEVICE, USER INTERFACE AND BLOOD TREATMENT APPARATUS FOR DETERMINING NEW ADJUSTABLE VALUES

(71) Applicants:Fresenius Medical Care Deutschland GmbH, Bad Homburg (DE); Fresenius Medical Care GmbH, Bad Homburg (DE)

(72) Inventors: Bernhard Karow, Rosbach (DE); Juergen Klewinghaus, Oberursel (DE)

(73) Assignees: Fresenius Medical Care Deutschland GmbH, Bad Homburg (DE); Fresenius Medical Care GmbH, Bad Homburg (DE)

( * ) Notice: Subject to any disclaimer, the term of this patent is extended or adjusted under 35 U.S.C. 154(b) by 842 days.

(21) Appl. No.: 17/775,668

(22) PCT Filed: Nov. 11, 2020

(86) PCT No.: PCT/EP2020/081732
§ 371 (c)(1),
(2) Date: May 10, 2022

(87) PCT Pub. No.: WO2021/094357
PCT Pub. Date:May 20, 2021

(65) Prior Publication Data
US 2022/0409796 A1      Dec. 29, 2022

(30) Foreign Application Priority Data
Nov. 12, 2019    (DE) ..................... 10 2019 130 432.6

(51) Int. Cl.
*A61M 1/36*              (2006.01)
(52) U.S. Cl.
CPC ..... *A61M 1/3607* (2014.02); *A61M 2205/502* (2013.01); *A61M 2230/20* (2013.01)

(58) Field of Classification Search
CPC .......... A61M 1/3607; A61M 2205/502; A61M 2230/20; A61M 1/3609; A61M 1/3672;
(Continued)

(56) References Cited

U.S. PATENT DOCUMENTS 5,378,227 A  *   1/1995  O'Riordan .......... A61M 1/3624
                                                                604/6.11
8,900,172 B2    12/2014  Pohlmeier
(Continued)

FOREIGN PATENT DOCUMENTS

DE        102011010406       8/2012
EP              2762179       8/2014
(Continued)

OTHER PUBLICATIONS

International Search Report and Written Opinion in International Appln. No. PCT/EP2020/081732, mailed Feb. 15, 2021, 19 pages (with English translation).

*Primary Examiner* — Philip R Wiest
*Assistant Examiner* — Brandon W. Levy
(74) *Attorney, Agent, or Firm* — Fish & Richardson P.C.

(57)                ABSTRACT
The present disclosure relates to a control device or closed-loop control device programmed to control or regulate a blood treatment apparatus during an administered treatment of a patient's blood using an extracorporeal blood tubing set and the blood treatment apparatus based on set adjustable values of treatment parameters set by using the blood treatment apparatus or using another device optionally connected to the extracorporeal blood tubing set, wherein the control device or closed-loop control device is further programmed, after reading, to compare at least one measurement value collected during the administered treatment, as the actual value of a blood parameter with a stored target value of the blood parameter. Based on this comparison and observation of a set adjustable value of one of the treatment parameters, either a correction value or correction factor to change the set adjustable value or a new adjustable value is determined in each case.

4 Claims, 2 Drawing Sheets

(58) Field of Classification Search
CPC ........ A61M 1/3406; A61M 2205/3306; A61M
2205/3334; A61M 1/1601; G01N 33/49
See application file for complete search history.

(56) References Cited

U.S. PATENT DOCUMENTS

| | | | |
|---|---|---|---|
| 9,022,966 B2 * | 5/2015 | Lannoy | A61M 1/3675 |
| | | | 604/6.07 |
| 9,278,171 B2 | 3/2016 | Brandl et al. | |
| 2007/0215545 A1 * | 9/2007 | Bissler | A61M 1/1613 |
| | | | 703/11 |
| 2008/0015487 A1 | 1/2008 | Szamosfalvi et al. | |
| 2011/0208105 A1 | 8/2011 | Brandl et al. | |
| 2011/0237996 A1 * | 9/2011 | Kotanko | A61M 1/16 |
| | | | 604/6.07 |
| 2015/0374897 A1 | 12/2015 | Favre | |
| 2017/0333623 A1 * | 11/2017 | Kamen | A61M 5/1408 |
| 2018/0110916 A1 * | 4/2018 | Xue | G01N 1/34 |
| 2018/0147335 A1 | 5/2018 | Nilsson | |

FOREIGN PATENT DOCUMENTS

| | | |
|---|---|---|
| JP | 2009-509584 | 3/2009 |
| JP | 2016-007541 | 1/2016 |
| WO | WO 2007/038347 | 4/2007 |
| WO | WO 2009/026603 | 3/2009 |
| WO | WO 2010/148194 | 12/2010 |

* cited by examiner

CONTROL DEVICE OR CLOSED-LOOP CONTROL DEVICE, USER INTERFACE AND BLOOD TREATMENT APPARATUS FOR DETERMINING NEW ADJUSTABLE VALUES

CROSS-REFERENCE TO RELATED APPLICATIONS

The present application is the national stage entry of International Patent Application No. PCT/EP2020/081732, filed on Nov. 11, 2020, and claims priority to Application No. DE 10 2019 130 432.6, filed in the Federal Republic of Germany on Nov. 12, 2019.

TECHNICAL FIELD

The present disclosure relates to a control device or closed-loop control device as described herein. Furthermore, it relates to a user interface as described herein and a blood treatment apparatus as described herein. It further relates to a digital storage medium as described herein, a computer program product as described herein, as well as a computer program as described herein.

BACKGROUND

During blood treatment sessions, on a blood treatment apparatus used for this purpose, previously set adjustable values for variable treatment parameters may be modified in certain circumstances by a user, e.g., clinic staff, to adjust the treatment to changeable, external conditions, the patient's condition or his (actual) values determined during the treatment (for example, his current blood values). The modification of such adjustable values may be prompted by the user, e.g., via a monitor (touchscreen) or at other interfaces.

SUMMARY

An object of the present disclosure is to propose a further control device or closed-loop control device for determining new adjustable values, also a further user interface, a further blood treatment apparatus, a further digital storage medium, a further computer program product as well as a further computer program.

The object of the present disclosure may be achieved with a control device or closed-loop control device having the features disclosed herein. It may be further achieved by a user interface having the features disclosed herein, as well as by a blood treatment apparatus having the features disclosed herein, also by a digital storage medium having the features disclosed herein, by a computer program product having the features disclosed herein and also by a computer program having the features disclosed herein.

The control device or closed-loop control device according to the present disclosure is programmed to control or to regulate a blood treatment apparatus during a treatment of the patient's blood. Such a treatment is or would be performed (usually using an extracorporeal blood tubing set or blood circuit and the blood treatment apparatus) based on one or more adjustable values (e.g., a current adjusted citrate dosage Ci-Konz_prev) of the treatment parameters (e.g., the citrate concentration or citrate dosage Ci-Konz). Such adjustable values can be or will be adjusted at the blood treatment apparatus or an optional device, connected to the extracorporeal blood tubing set.

The control device or closed-loop control device is further programmed to read (for example into a calculation device)

as its actual value at least one measurement value of a blood parameter, usually collected during the blood treatment, (for example a calcium concentration or calcium dosage of the blood, in short: Ca-Konz).

The measurement value may have been obtained by analysing blood in a laboratory. The blood may have been obtained from the patient during the blood treatment session using a needle or needle-free (e.g., by taking the sample from the guided extracorporeal blood in the extracorporeal blood circuit). Such samples may be taken multiple times during a current blood treatment session and analysed with the same objective.

It is further programmed to compare this actual value with a target value of this blood parameter (for example Ca-Konz), stored on the machine side, for example, in the control device or closed-loop control device or a storage device.

It is further programmed to determine, select or read-in, directly at this blood treatment apparatus used for the treatment, the set adjustable value of one of the treatment parameters (for example, the Ci-Konz mentioned above), for example, from current settings on the blood treatment apparatus adjusted for the ongoing treatment.

It is in turn further programmed to determine either a correction value or a correction factor (e.g., Ci-Konz_korr) for the set adjustable value (Ci-Konz_prev), also referred to as correction factor for short, (alternative a)), or a new adjustable value (e.g., Ci Konz_new) (alternative b)).

The correction value or correction factor (e.g., Ci-Konz_korr) determined in alternative a) serves to change, based on this value, the set adjustable value (Ci-Konz_prev) of the treatment parameter (Ci-Konz), which is intended to cause a change of the current value or the current level of the blood parameter towards its target value, or for example, a change in the blood parameter from a current value, whether measured or not, towards its target value.

In alternative b) the control device or closed-loop control device may be programmed to immediately determine a new adjustable value (e.g., Ci-Konz_new) for controlling or regulating the blood treatment apparatus with the new adjustable value (Ci-Konz_new), its application would also result in changing the current value or the current level of the blood parameter towards its desired target value or, for example, changing the blood parameter from a current value, whether measured or not, towards its target value.

The desired change in the blood parameter should be such that, in the course of the further treatment of the patient, the actual value will change preferably towards its target value. The correction value or the new adjustable value is thereby determined based on both the determined actual value and on the desired or stored target value.

The control device or closed-loop control device is further programmed in each case to determine the new adjustable value (e.g., Ci-Konz_new) and optionally, to automatically provide it in the control device or closed-loop control device, in order to control or regulate the blood treatment apparatus—such as at a later time—using the new adjustable value (Ci-Konz_new).

The provision of the new adjustable value may be understood as its—e.g., temporary—storage, such as in a RAM (random access memory). The provision is preferably not to be understood as meaning that the control device or closed-loop control device automatically begins the treatment using the new adjustable value without being prompted or authorized to do so, for example, by the user. However, if the blood treatment apparatus is prompted e.g., by the user, to continue the treatment using the new adjustable value, this is already available machine side for the control device or closed-loop control device.

The term "adjustable value" herein may include the term "dose value"

The user interface according to the present disclosure is in signal communication with a control device or closed-loop control device, such as one according to the present disclosure.

The blood treatment apparatus according to the present disclosure includes a control device or closed-loop control device according to the present disclosure, or/and a user interface according to the present disclosure, or it is at least connected to these or such apparatuses, e.g., in signal communication. Control device or closed-loop control device and/or the user interface may be provided to control or regulate the treatment via the blood treatment apparatus.

A digital non-volatile storage medium, according to the present disclosure, such as in the form of a machine readable medium, such as in the form of a disk, CD, DVD EPROM, FRAM (Ferroelectric RAM) or SSD (Solid-State-Drive), such as with electrically or optically readable control signals, can interact with a programmable computer system, so that a control device or closed-loop control device can be programmed to be a control device or closed-loop control device according to the present disclosure.

A computer program product, according to the present disclosure, includes a volatile or transient program code or one stored on a machine readable carrier or a signal wave, to interact in such a way with a programmable computer system so that a control device or closed-loop control device can be reprogrammed to be a control device or closed-loop control device according to the present disclosure. Computer program product, for example, can be understood according to the present disclosure as a computer program stored on a carrier, an embedded system being a comprehensive system with a computer program (e.g., an electronic device with a computer program), a network of computer implemented computer programs (e.g., a client/server-system, a cloud computing system etc.), or a computer on which a computer program is loaded, runs, is stored, is being executed or developed.

The term "machine readable carrier" as is as used herein, refers in certain embodiments of the present disclosure to a carrier, which contains data or information interpretable by software and/or hardware. The carrier may be a data carrier, such as a diskette, a CD, DVD, a USB stick, a flashcard, an SD card or the like, as well as any other storage referred to herein or any other storage medium referred to herein.

A computer program according to the present disclosure includes a program code, so that a control device or closed-loop control device can be programmed to be a control device or closed-loop control device according to the present disclosure if the computer program is running on a corresponding computer. According to the present disclosure, computer program can be understood for example, to be a physical, ready-to-distribute software-product, which includes a program.

In all of the aforementioned or following statements, the use of the expression "may be" or "may have" and so on, is to be understood synonymously with "preferably is" or "preferably has," and so on respectively, and is intended to illustrate embodiments according to the present disclosure.

Embodiments according to the present disclosure may include one or several of the aforementioned or following features. In this, the features mentioned herein may, in any combination, be subject-matter of embodiments according to the present disclosure, unless the person skilled in the art recognizes a specific combination as technically impossible.

Furthermore, embodiments according to the present disclosure are subject-matter of the claims following this disclosure.

Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" as encompassing "at least one". This understanding is also equally encompassed by the present disclosure as the interpretation that a numeric word, for example, "one" may alternatively mean "exactly one", wherever this is evidently technically possible for the person skilled in the art. Both are encompassed by the present disclosure and apply herein to all used numerical words.

Whenever an applicability or a method step is mentioned, embodiments of the present disclosure also include the corresponding programming or configuring of a suitable apparatus or a section thereof.

Whenever an embodiment is mentioned herein, it is then an exemplary embodiment according to the present disclosure. The statements "top" and "bottom" are to be understood here in case of doubt by the person skilled in the art as absolute or relative space indications, which relate to the orientation of the relevant component during its intended use.

In some embodiments of the control device or closed-loop control device according to the present disclosure the determining of the correction value or correction factor (e.g., Ci-Konz_korr) or of the new adjustable value (e.g., Ci-Konz_new) is or encompasses referring back to saved values. These can be in the form of a table, for example. The determining may be or include calculation and/or the like.

In several embodiments, in determining the correction value or correction factor (e.g., Ci-Konz_korr) or the new adjustable value (e.g., Ci-Konz_new) information may be included about how much time has passed since the last change of the adjustable value. Provision may then be made to treat the patient immediately using the new value, as soon as it is accepted. Alternatively, however, damping, delay or attenuation may be facilitated so that the new adjustable value is at first delayed and/or comes into effect gradually or is used gradually during the patient's treatment. Thus, provision may be made that the smaller the time period which has elapsed since the adjustable value was last changed, the later the new setting value fully comes into effect, or vice versa.

In several embodiments, it may be taken into account when determining via which measurement value method and/or via which measuring device the measurement value has been collected.

In some embodiments, the measurement value corresponds to a calcium concentration value, such as ionized calcium, in the blood of the patient. For example, the measurement value corresponds to a concentration or a concentration value of calcium in that blood of the patient which has been taken from or is present in the extracorporeal blood circuit, such as the venous section or downstream of a blood filter.

The measurement value can be regarded as up-to-date for the purpose of the present disclosure, even if time has elapsed since it was collected, for example for its processing.

In some embodiments, the treatment parameter is or encompasses a concentration of citrate in the blood of the patient, such as in the blood present in the extracorporeal blood tubing set, such as in the arterial section or upstream of a blood filter. Similarly, the treatment parameter may be a citrate concentration of a citrate-containing solution added to the blood, or its flow or rate (e.g., in ml/min).

In some embodiments, the control device or closed-loop control device according to the present disclosure for controlling or regulating the blood treatment apparatus, is programmed based on the correction value or correction factor (e.g., Ci-Konz_korr) or the new adjustable value (e.g., Ci-Konz_new), preferably without having to transmit or input these to the blood treatment apparatus, such as via a user interface. Preferably, the controlling or regulating of the blood treatment apparatus is based on the correction value or correction factor (e.g., Ci-Konz_korr) or the new adjustable value (e.g., Ci-Konz_new) but only after the user has confirmed this value.

In some embodiments, the control device or closed-loop control device according to the present disclosure is programmed to control or regulate the blood treatment apparatus based on the new, changed adjustable value (Ci-Konz_new) of the treatment parameter, preferably automatically. Preferably, the control or regulation of the blood treatment apparatus is based on the changed, new adjustable value (Ci-Konz_new) of the treatment parameter but only after the user has confirmed the changed adjustable value.

The confirmation may simply be the operation of an "OK" button or the like.

Confirmation, in several embodiments, does not include typing, entering, selecting, etc. of adjustable values from a variety of options, nor even mental arithmetic.

In several embodiments, the correction value or correction factor come from a comparison table stored in the control device or closed-loop control device or in a storage device. How much the actual value deviates from the target value and which correction is proposed in each case can preferably be worked out from this table. The same can optionally apply to the new adjustable value. It too, can also be determined from tables.

In some embodiments, the new adjustable value is calculated from the last set adjustable value and the correction value or correction factor, e.g., via subtraction or addition. In some embodiments, the user interface according to the present disclosure includes at least one first input interface to enter the measurement value—usually measured during the blood treatment—as an actual value (e.g., Ca++—Ist) by the user. This actual value may have been determined by measurement in the laboratory, e.g., after a blood withdrawal.

The first input interface can be a correspondingly connected touch screen, a rotary switch, a slide, a keyboard, a network interface to a computer system at the doctors' practice, the clinic or the hospital or the like.

The first input interface can additionally or alternatively include a network interface, via which, for example, a Ca++—actual value can be taken from a storage device of the network, e.g., the clinic. For example, measurement values that an examination unit such as a BGA—(blood gas analysis) device transmits to the network, can be stored in conjunction with, for example, data to identify the associated patient, such as his ID, name, barcode and/or the like. Such provided measurement values could be taken on automatically or manually via the network interface, which can further simplify the input process.

In several embodiments the user interface according to the present disclosure includes a first output interface, via which the correction value or correction factor (e.g., Ci-Konz_korr) or the adjustable value changed or corrected on the basis of the correction value can be displayed as a new adjustable value for the attention of the user. The output interface may be, for example, a correspondingly stored or configured display area (window) of a monitor, touch screen or the like.

In some embodiments, the user interface according to the present disclosure has at least one second input interface, configured so that the user may confirm, the given correction value or correction factor (e.g., Ci-Konz_korr) or the changed or corrected adjustable value based on the correction value, as a new adjustable value via this interface. This can be achieved, for example, by offering two buttons (e.g., "yes"/"no" or "OK"/"C").

The second input interface may be configured like the first input interface, or differently. The first input interface and the second input interface may be present in a common unit, such as portions of the same touch screen.

In several embodiments the blood treatment apparatus according to the present disclosure is designed as a dialysis apparatus, a hemodialysis apparatus, hemofiltration apparatus or hemodiafiltration apparatus, such as an apparatus for chronic renal replacement therapy or for continuous renal replacement therapy (CRRT).

Other treatment parameters may include, for example, the concentration at which calcium is supplied to the blood, e.g., from a source of calcium solution, a dialysis liquid rate (or flow), a blood delivery rate, etc.

Further blood parameters can be parameters of the acid/base balance of the patient or his blood.

Whenever "programmed" or "configured" is mentioned herein, it is to be understood that these terms are interchangeable.

Several or all embodiments according to the present disclosure may include one, more or all of the advantages mentioned above and/or in the following.

An advantage of the present disclosure may be that it considerably simplifies the adaptation of treatment parameters (i.e., the changing of adjustable values), for example the correction of the set dosage of anticoagulants such as, e.g., citrate. This simplification can be advantageously used to give, for example, the inexperienced user more security when giving or setting a desired dosage.

The probability of error during the adaptation of treatment parameters can be significantly reduced, for example because mental calculation steps and/or input errors such as typing errors made by the user can be eliminated.

This means that indirectly the patient's safety may also be advantageously increased.

The competence responsibility for changing the adjustable values, can however advantageously remain with the user if, for example, the control device or closed-loop control device requests a confirmation from the user, and the change of the adjustable value only takes place after positive confirmation by the user. The user thus receives valuable support from the control device or closed-loop control device according to the present disclosure, but without being surprised by it acting of its own volition.

BRIEF DESCRIPTION OF THE FIGURES

The present disclosure is exemplarily explained with regard to the accompanying drawings in which same reference numerals refer to the same or similar elements. The following applies in the partly highly simplified figures: In the figures of the drawing the following applies.

DETAILED DESCRIPTION

Figure 1:
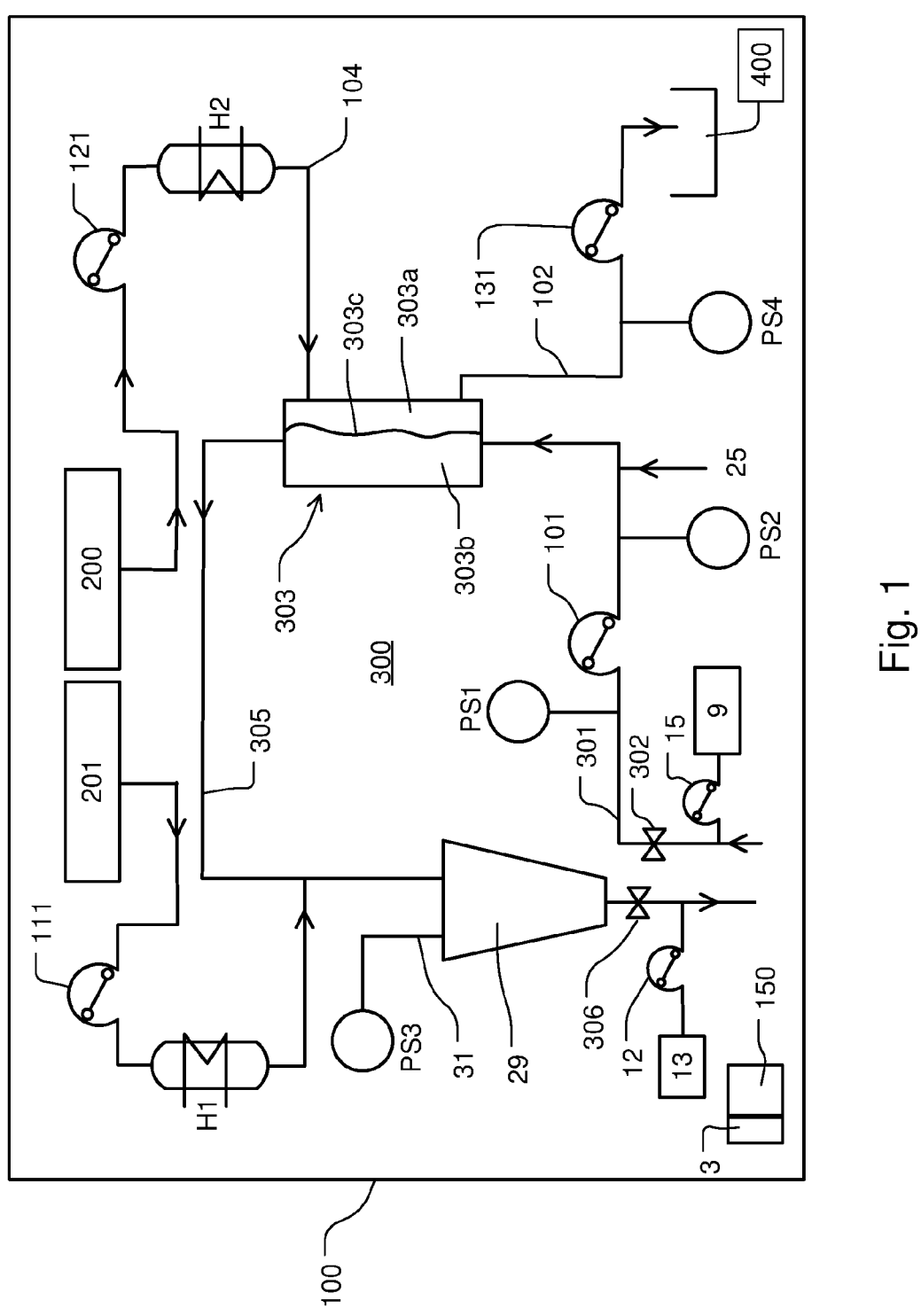
FIG. 1 shows in a highly simplified representation a process flow chart of a blood treatment apparatus according to the present disclosure.

FIG. 1 shows in a highly simplified representation a process flow chart of a blood treatment apparatus 100 according to the present disclosure, optionally connected to an extracorporeal blood circuit 300.

The extracorporeal blood circuit 300 includes a first line 301, here in the form of an arterial line section.

The first line 301 is in fluid connection with a blood treatment device, here exemplarily, a blood filter or dialyzer 303. The blood filter 303 includes a dialysis liquid chamber 303*a* and a blood chamber 303*b,* which are separated from each other by a mostly semi-permeable membrane 303*c.*

The extracorporeal blood circuit 300 further includes at least one second line 305, here in the form of a venous line section. Both the first line 301 as well as the second line 305, can serve to be connected to the vascular system of the patient, not shown.

The first line 301 is optionally connected to a (first) tube clamp 302 for blocking or closing the line 301. The second line 305 is optionally connected to a (second) tube clamp 306 for blocking or closing the line 305.

The blood treatment apparatus 100 represented in FIG. 1 schematically and only by some of its devices, includes a blood pump 101. During the patient's treatment the blood pump 101 conveys blood through sections of the extracorporeal blood circuit 300 and in the direction of the blood filter or dialyzer 303 as shown by the small arrows, which generally indicate in each of the figures the direction of flow.

Using a pump for dialysis liquid 121, that may be embodied as a roller pump or as any otherwise occluding pump, fresh dialysis liquid is pumped from a source 200 along the dialysis liquid inlet line 104 into the dialysis liquid chamber 303*a*. The dialysis liquid leaves the dialysis liquid chamber 303*a* as dialysate, possibly enriched with filtrate, in the direction of the effluent bag 400 and will be referred to herein as effluent.

The source 200 may for example be a bag or a container. The source 200 may further be a fluid line, for example, a hydraulic outlet or hydraulic port of the blood treatment apparatus 100, from which the online and/or continuously generated or mixed liquid is provided.

A further source 201 with substituate may optionally be provided. It may correspond to the source 200 or be a separate source.

A schematically shown control device or closed-loop control device 150 can be configured to control or regulate the blood treatment session.

Where the effluent bag 400 connects to the blood treatment apparatus 100 is indicated in the bottom right of FIG. 1.

In addition to the aforementioned blood pump 101, the arrangement shown in FIG. 1 further includes, purely optionally, a number of other optional pumps, namely the pump 111 for substituate, the pump 121 for dialysis liquid and the pump 131 for the effluent.

The pump 121 is provided to supply dialysis liquid to the blood filter 303, from a source 200, for example a bag, through an optional available bag heater H2 having a heat pack, using the dialysis liquid inlet line 104.

The thus supplied dialysis liquid exits from the blood filter 303 via a dialysate outlet line 102, aided by the pump 131, and may be discarded.

An optional arterial sensor PS1 is provided upstream of the blood pump 101. It measures the pressure in the arterial line during a patient's treatment.

A further optional pressure sensor PS2 is provided downstream of the blood pump 101, but upstream of the blood filter 303 and if provided, upstream of an addition point °25 for Heparin. It measures the pressure upstream of the blood filter 303 ("pre-hemofilter").

To measure the filtrate pressure of the blood filter 303 a further pressure sensor may be provided as PS4 downstream of the blood filter 303, however, preferably upstream of the pump 131 in the dialysate outlet line 102.

Blood, which leaves the blood filter 303, passes through an optional venous blood chamber 29, which may include a ventilation device 31 and/or a further pressure sensor PS3.

The control device or closed-loop control device 150 shown in FIG. 1 may be in wired or wireless signal connection to any of the components referred to herein—such as to the blood pump 101—in order to control or regulate the blood treatment apparatus 100.

The optional pump 111 is provided to supply substituate from the optional source 201, for example a bag, via an optional available bag heater H1 having a heat pack, to the second line 305.

In several embodiments a citrate solution is dispensed from an optionally provided source for citrate solution, here exemplarily embodied as a citrate bag 9, into the first line 301, optionally by a citrate pump 15. For example, 4%-iges $Na_3Citrat$ is added from the citrate solution source.

An optional feed device, embodied herein as a calcium pump 12, is provided to supply a calcium solution from an optional source for calcium solution, embodied, for example, in FIG. 1 as a calcium bag 13, into the line 305. For example, a $CaCl_2$-solution is supplied from the source of calcium solution. This may have a calcium concentration of 91 mmol/l, 100 mmol/l or another and/or comparable calcium concentration.

Figure 2:
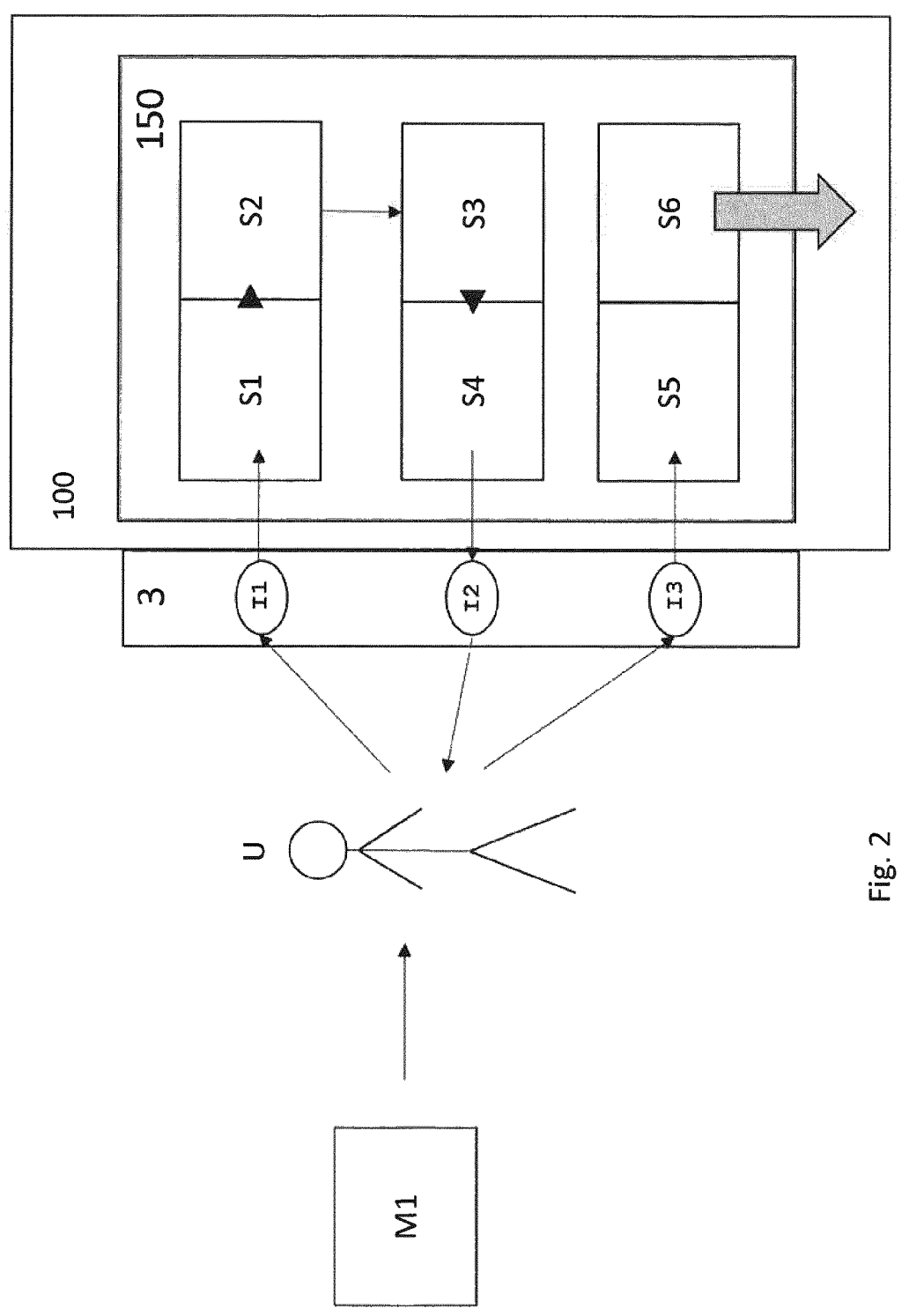
FIG. 2 shows in a schematic representation the course of a method using an embodiment of a control device or closed-loop control device according to the present disclosure.

FIG. 2 schematically shows, the sequence of a method initiated by a control device or closed-loop control device 150 according to the present disclosure of a blood treatment apparatus 100 in an exemplary embodiment. This example relates to anticoagulation using citrate and calcium, without limiting the disclosure thereto.

Hereby M1 corresponds to a measurement value, for example a blood parameter which was not determined by the blood treatment apparatus 100 nor by the control device or closed-loop control device 150, but is the actual value of the blood parameter, which was determined, e.g., in the laboratory based on a blood sample. M1 may be, for example, a measured calcium concentration Ca++_Ist. The measurement value M1 is known to a user U.

The user U may enter the measurement value M1 for example, via a first input interface of a user interface 3 and allow it to be read by the control device or closed-loop control device 150, wherein the user interface 3 may be part of the control device or closed-loop control device 150, the blood treatment apparatus 100 or another apparatus. Alternatively the control device or closed-loop control device 150 automatically reads the measurement value M1.

This reading step is indicated by S1 in FIG. 1.

The user U may have the current adjustable value, for example, Ci Konz_prev checked upon request.

Optional plausibility checks via the control device or closed-loop control device 150, are possible at any point when entering data and/or values or when calculating other values, for example, and may also be encompassed in the present disclosure.

In a step S2 the read-in actual value Ca++_Ist is compared with target values Ca++_Soll of the blood parameter Ca-Konz, e.g., stored in the machine.

If a difference is detected between actual value and target value, either a correction value or correction factor Ci-Konz_korr or a proposal for a new adjustable value Ci-Konz_new will be calculated now in a step 3 based on a set adjustable value Ci-Konz_prev and on the values determined in step S2. Using these newly calculated values, it is possible in each case to work towards a change in the future actual values of the blood parameter Ca-Konz in the direction of its target value Ca++_Soll, e.g., using the citrate pump 15. When determining a correction value or Ci-Konz_korr this is achieved by changing the set adjustable value Ci-Konz_prev, when determining a new adjustable value Ci-Konz_new, this is achieved by replacing the previously set adjustable value Ci-Konz_prev with the new adjustable value for the further course of the treatment, as further explained in the following with regard to step S4.

In the optional step S4, the output of the value calculated in S3, therefore that of either the correction value or Ci-Konz_korr or of the new adjustable value Ci-Konz_new, is initiated via an output interface I2 for acknowledgment and/or confirmation by the user U.

Purely as an example, in this embodiment a confirmation is requested from the user U via a second input interface I3. The step S5 represents an evaluation and possibly a further processing of this second input, which may be for example "yes" or "no", "ok" or "C".

In step S6, the new adjustable value (Ci-Konz_new) is, upon request, automatically provided in the control device or closed-loop control device 150 for controlling and regulating the blood treatment apparatus 100, based on the new adjustable value Ci-Konz_new for further treatment, such as until a new change, indicated using the wide arrows in the direction of the blood treatment apparatus 100 (the request may be the accepting of the new adjustable value Ci-Konz_new by the user U).

In the present embodiment the control device or closed-loop control device 150 according to the present disclosure is exemplarily represented as a section of the blood treatment apparatus 100. Embodiments of the present disclosure also include other like arrangements, for example, separately at, on and/or next to the blood treatment apparatus 100.

The aforementioned exemplary embodiment relates to the measurement of calcium as a blood parameter and the dosage of citrate as an adjustable value. However, the present disclosure is by no means limited to this.

LIST OF REFERENCE NUMERALS

3 user interface
9 source for citrate solution, here, e.g., a citrate bag
12 calcium pump
13 source for calcium solution, calcium bag
150 citrate pump
25 addition point for Heparin (optional)
29 venous blood chamber (optional)
31 ventilation/venting, de-aeration or de-airing device
100 blood treatment apparatus
101 blood pump
102 dialysate outlet line, effluent inlet line

104 dialysis liquid inlet line
111 pump for substituate
121 pump for dialysis liquid
131 pump for dialysate or effluent in effluent inlet line
150 control device or closed-loop control device
200 dialysis liquid source
201 substituate source, optional
300 extracorporeal blood circuit
301 first line (arterial line section)
302 (first) tube clamp
303 blood filter or dialyzer
303*a* dialysis liquid chamber
303*b* blood chamber
303*c* semi-permeable membrane
305 second line (venous line section)
306 (second) tube clamp
M1 measurement value of a blood parameter
I1 first input interface
I2 output interface
I3 second input interface
S1 reading of input
S2 comparing of input with other values
S3 calculation of a proposal or recommendation
S4 giving/displaying of a proposal or recommendation
S5 processing of the confirmation
S6 accepting/carrying out of the proposal/recommendation
U user; clinic personnel

The invention claimed is:

1. A blood treatment apparatus comprising a control device or closed-loop control device programmed to control or to regulate a blood treatment apparatus during an administered anticoagulation treatment of a patient's blood using an extracorporeal blood tubing set and the blood treatment apparatus based on set adjustable values of treatment parameters that are set at the blood treatment apparatus or at an optional device connected to the extracorporeal blood tubing set, wherein the control device or closed-loop control device is further programmed for:

reading at least one measurement value of a blood parameter collected during the administered anticoagulation treatment as the actual value of the blood parameter, wherein the at least one measurement value comprises a concentration of calcium in the patient's blood, wherein the control device or closed-loop control device is configured to control a calcium pump to supply a calcium solution as part of the administered anticoagulation treatment, and wherein the control device or closed-loop control device is configured to control a citrate pump to supply a citrate solution as part of the administered anticoagulation treatment;

comparing the actual value with a stored target value of the blood parameter;

determining a set adjustable value of a treatment parameter; and either:

determining a correction value or correction factor to change the set adjustable value of the treatment parameter in order to change the actual value of the blood parameter towards its stored target value based on actual values and target values and an automatic provision of a new adjustable value in the control device or closed-loop control device to control or regulate the blood treatment apparatus based on the new adjustable value upon request, or determining a new adjustable value in order to change the actual value of the blood parameter towards its target value based on the actual values and target values and the automatic provision of the new adjustable value in the control device or closed-loop control device to control or regulate the blood treatment apparatus based on the new adjustable value upon request, wherein the control device or closed-loop control device is configured such that the automatic provision of the new adjustable value does not cause the control device or closed-loop control device to automatically start the administered anticoagulation treatment, wherein the control device or closed-loop control device is programmed to control or regulate the blood treatment apparatus based on the correction value, the correction factor, or the new adjustable value after a confirmation by a user, such that the user is permitted to provide a request, and the control device or closed-loop control device is configured to respond to the request, before the administered anticoagulation treatment is started based on the automatic provision of the new adjustable value to maintain an ultimate responsibility of implementing the new adjustable value with the user, wherein the blood treatment apparatus further comprises:

the calcium pump, configured to supply the calcium solution as part of the administered anticoagulation treatment; and

the citrate pump, configured to supply the citrate solution as part of the administered anticoagulation treatment, and wherein an implementation of the correction value or correction factor or the new adjustable value is delayed such that:

the smaller a time period which has elapsed since the set adjustable value was last changed, the later a new setting value fully comes into effect, or the larger the time period which has elapsed since the set adjustable value was last changed, the sooner the new setting value fully comes into effect.

2. The blood treatment apparatus according to claim 1, wherein the blood treatment apparatus comprises a dialysis apparatus, a hemodialysis apparatus, a hemofiltration apparatus, or a hemodiafiltration apparatus.

3. The blood treatment apparatus according to claim 1, wherein the blood treatment apparatus is an apparatus for chronic renal replacement therapy or for continuous renal replacement therapy (CRRT).

4. The blood treatment apparatus according to claim 1, further comprising a user interface connected in signal communication to the control device or closed- loop control device.

* * * * *